(12) United States Patent  
Niemimäki

(10) Patent No.: US 8,880,377 B2  
(45) Date of Patent: Nov. 4, 2014

(54) OVERALL MOTION DETERMINATION

(75) Inventor: Mika Niemimäki, Haukipudas (FI)

(73) Assignee: Polar Electro Oy, Kempele (FI)

( * ) Notice: Subject to any disclaimer, the term of this patent is extended or adjusted under 35 U.S.C. 154(b) by 413 days.

(21) Appl. No.: 13/139,541

(22) PCT Filed: Dec. 22, 2008

(86) PCT No.: PCT/FI2008/050782  
§ 371 (c)(1),  
(2), (4) Date: Jul. 7, 2011

(87) PCT Pub. No.: WO2010/072883  
PCT Pub. Date: Jul. 1, 2010

(65) Prior Publication Data

US 2011/0264401 A1    Oct. 27, 2011

(51) Int. Cl.
| | |
|---|---|
| G01C 25/00 | (2006.01) |
| A61B 5/11 | (2006.01) |
| A61B 5/00 | (2006.01) |
| G01C 22/00 | (2006.01) |
| A61B 5/0205 | (2006.01) |
| A61B 5/024 | (2006.01) |
| A63B 24/00 | (2006.01) |
| A63B 69/00 | (2006.01) |

(52) U.S. Cl.  
CPC ............. *A61B 5/1123* (2013.01); *A61B 5/6825* (2013.01); *A61B 5/6829* (2013.01); *G01C 22/006* (2013.01); *A61B 5/0002* (2013.01); *A61B 5/0205* (2013.01); *A61B 5/024* (2013.01); *A61B 5/6824* (2013.01); *A61B 2562/0219* (2013.01); *A63B 24/0062* (2013.01); *A63B 69/0028* (2013.01); *A63B 2220/12* (2013.01); *A63B 2220/22* (2013.01); *A63B 2220/30* (2013.01); *A63B 2220/40* (2013.01); *A63B 2225/50* (2013.01); *A63B 2230/06* (2013.01); *A63B 2230/75* (2013.01)  
USPC .......................................................... 702/141

(58) Field of Classification Search  
CPC ................................ G01P 15/00; G01C 25/00  
USPC .......................................................... 702/141  
See application file for complete search history.

(56) References Cited

U.S. PATENT DOCUMENTS

| | | | |
|---|---|---|---|
| 4,625,733 A | 12/1986 | Saynajakangas | |
| 6,145,389 A * | 11/2000 | Ebeling et al. | 73/865.4 |
| 6,305,221 B1 * | 10/2001 | Hutchings | 73/488 |
| 6,522,266 B1 | 2/2003 | Soehren et al. | |
| 2002/0040601 A1 | 4/2002 | Fyfe et al. | |
| 2008/0214360 A1 | 9/2008 | Stirling et al. | |
| 2008/0234933 A1* | 9/2008 | Chowdhary et al. | 701/213 |

FOREIGN PATENT DOCUMENTS

EP    1066793 A2    1/2001

OTHER PUBLICATIONS

Tuomo Reiniaho, International Search Report from corresponding International Application No. PCT/FI2008/050782, pp. 1-11, Finland (2009).

* cited by examiner

*Primary Examiner* — Jonathan C Teixeira Moffat  
*Assistant Examiner* — Joseph J Yamamoto  
(74) *Attorney, Agent, or Firm* — Hoffmann & Baron, LLP

(57) ABSTRACT

An apparatus, a method, and a computer program are disclosed. The apparatus comprises a processor. The processor is configured to obtain instantaneous acceleration values representing lower limb motion of a user, to form an effective acceleration value from the instantaneous acceleration values over a plurality of steps of the user, and to determine a motion parameter representing overall motion of the user by means of the effective acceleration value.

17 Claims, 8 Drawing Sheets

US 8,880,377 B2

OVERALL MOTION DETERMINATION

CROSS-REFERENCE TO RELATED APPLICATION

This application is a National Phase application of International Application No. PCT/FI2008/050782, filed Dec. 22, 2008, which is incorporated by reference herein in its entirety.

BACKGROUND

1. Field

The invention relates to overall motion determination of a user by means of acceleration measured from lower limb motion of the user.

2. Description of the Related Art

The overall motion determination of the user may be used for various purposes, such as counting steps, measuring energy expenditure, and determining the user's speed and/or distance. Further improvements in overall motion determination are desirable, as consumer demand for devices implementing such functionality is growing rapidly.

SUMMARY

The present invention seeks to provide an improved apparatus, an improved method, and an improved computer program.

According to an aspect of the present invention, there is provided an apparatus as specified in claim 1.

According to another aspect of the present invention, there is provided a method as specified in claim 7.

According to another aspect of the present invention, there is provided a computer program as specified in claim 12.

According to another aspect of the present invention, there is provided another apparatus as specified in claim 13.

According to another aspect of the present invention, there is provided another computer program as specified in claim 14.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an" embodiment in several locations, this does not necessarily mean that each such reference is to the same embodiment(s), or that the feature only applies to a single embodiment. Single features of different embodiments may also be combined to provide other embodiments.

Figure 10:
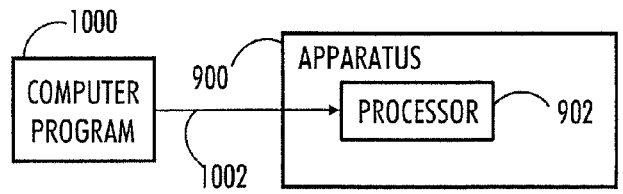
FIGS. 9, 10 and 11 illustrate embodiments of an apparatus.
Figure 9:
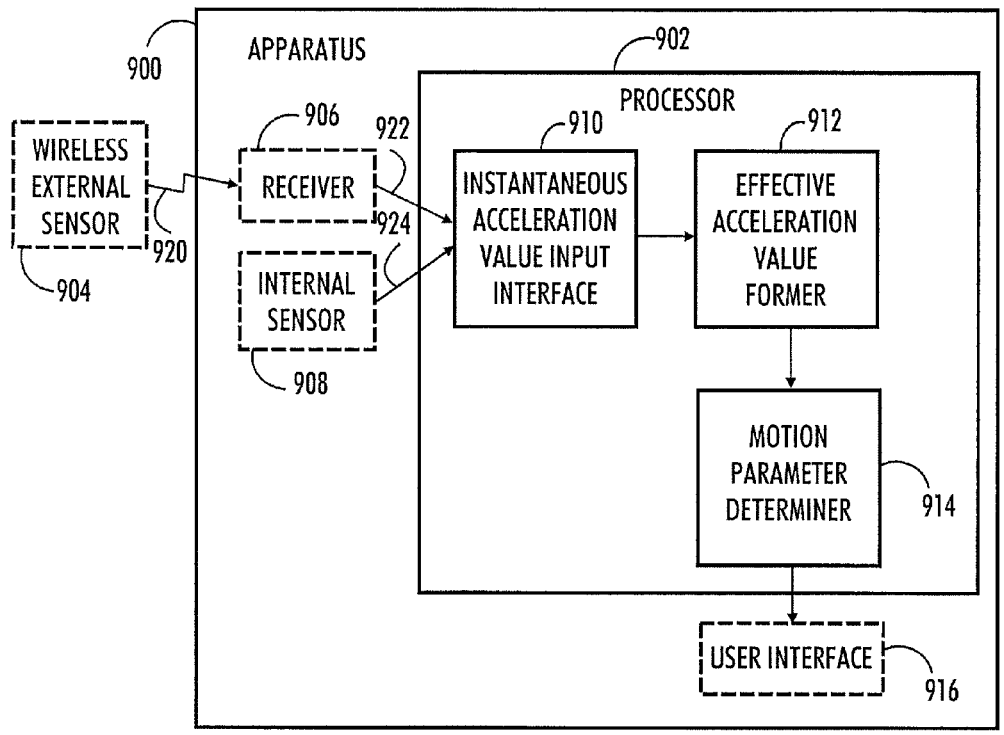
Figure 11:
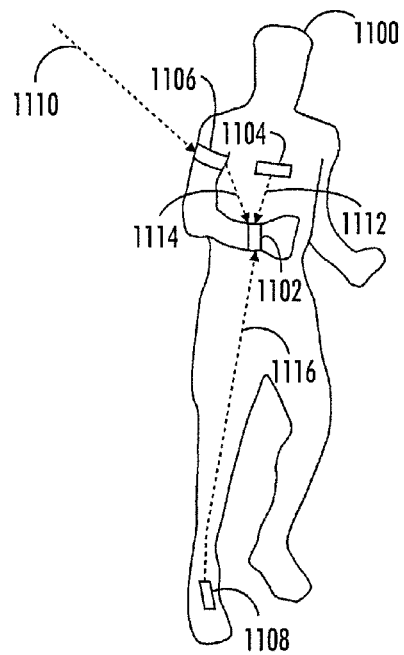

FIGS. 9 to 11 only show some elements whose implementation may differ from what is shown. The connections shown in FIGS. 9 to 11 are logical connections; the actual physical connections may be different. Interfaces between the various elements may be implemented with suitable interface technologies, such as a message interface, a method interface, a sub-routine call interface, a block interface, or any means enabling communication between functional sub-units. It should be appreciated that apparatuses may comprise other parts. However, such other parts may be irrelevant to the actual invention and, therefore, they need not be discussed in more detail here. It is also to be noted that although some elements are depicted as separate ones, some of them may be integrated into a single physical element. The specifications of apparatuses 900 develop rapidly. Such development may require extra changes to an embodiment. Therefore, all words and expressions should be interpreted broadly, and they are intended to illustrate, not to restrict, the embodiments.

FIG. 9 illustrates an apparatus 900. The apparatus 900 may be a mobile apparatus, a sports computer, a running computer, a multi-sports computer, an activity monitor, a pedometer, a foot-pod, a shoe-mounted stride sensor, a measurement unit attachable to a lower limb of the user, and/or a subscriber terminal of a radio system (such as a mobile phone), for example. The term 'mobile apparatus' 900 refers to a device that a user may move around. The apparatus 900 may be worn around the wrist, like a watch, for example. Polar Electro® (www.polarelectro.com) designs and manufactures such apparatuses 900 and their accessories. At the time of filing this patent application, the apparatus 900 may be implemented based on a Polar multi-sport sports computer RS800CX with a stride sensor, for example. The implementation of the embodiments in such an existing product requires relatively small and well-defined modifications. Naturally, as the products evolve, feasible platforms for the implementation of the embodiments described in this patent application also evolve and emerge.

The apparatus 900 may be a heart rate monitor for measuring the user's heart rate and possibly other physiological parameters that can be measured from the user. In U.S. Pat. No. 4,625,733, which is incorporated herein by reference, Säynäjäkangas describes a wireless heart rate monitoring concept where a transmitter attached to the user's chest measures the user's heart rate and transmits heart rate information telemetrically to a heart rate receiver attached to the user's wrist.

Other implementations may also be possible. The heart rate monitor may also be implemented such that the heart rate is directly measured from the wrist on the basis of pressure or optical measurement, for example. Other ways for measuring the heart rate may also be employed. As sensor technology becomes more integrated, less expensive, and its power consumption characteristics are improved, a sensor measuring heart activity data may also be placed in other arrangements besides the chest strap transmitter. Polar Electro is already marketing apparels which comprise integrated electrode structures.

FIG. 11 illustrates an embodiment where the apparatus 900 is implemented as a running computer such as Polar RS800. A runner 1100 is provided with the following equipment: a wrist receiver 1102, a heart rate transmitter 1104, an upper-arm-mounted positioning receiver 1106, and a shoe-mounted stride sensor 1108. The accessories 1104, 1106, 1108 communicate 1112, 1114, 1116 wirelessly with the wrist receiver 1102.

The positioning receiver 1106 receives 1110 external location information. The positioning receiver 1106 may be a receiver of a global navigation satellite system. Such a system may be the Global Positioning System (GPS), the Global Navigation Satellite System (GLONASS), the Galileo Positioning System (Galileo), the Beidou Navigation System, or the Indian Regional Navigational Satellite System (IRNSS), for example. The positioning receiver 1106 determines its location (longitude, latitude, and altitude) using signals 1110 transmitted from satellites orbiting Earth. Besides global navigation satellites, the positioning receiver 1106 may also determine its location utilizing other known positioning techniques. It is well known that by receiving radio signals from several different base stations, the mobile phone may determine its location.

The apparatus 900 may comprise a user interface 916. The user interface 916 may comprise a display, means for producing sound, and a keyboard and/or a keypad. The display may be a liquid crystal display, for example, but it may also be implemented by any appropriate prior art technique. The means for producing sound may be a loudspeaker or a simpler means for producing beeps or other sound signals. The keyboard/keypad may comprise a complete qwerty keyboard, a mere numeric keypad or only a few push buttons and/or rotary buttons. In addition, the user interface 916 may comprise other prior art user interface elements, for example various means for focusing a cursor (mouse, track ball, various arrow keys, etc.) or elements enabling audio control. A motion parameter, such as a speed of the user and/or a travelled distance of the user may be shown on the user interface 916, on the display, for example.

The apparatus 900 comprises a processor 902. The term 'processor' refers to a device that is capable of processing data. The processor 902 may comprise an electronic circuit implementing the required functionality, and/or a microprocessor running a computer program implementing the required functionality. When designing the implementation, a person skilled in the art will consider the requirements set for the size and power consumption of the apparatus, the necessary processing capacity, production costs, and production volumes, for example.

The electronic circuit may comprise logic components, standard integrated circuits, application-specific integrated circuits (ASIC), and/or other suitable electronic structures.

The microprocessor implements functions of a central processing unit (CPU) on an integrated circuit. The CPU is a logic machine executing a computer program, which comprises program instructions. The program instructions may be coded as a computer program using a programming language, which may be a high-level programming language, such as C, or Java, or a low-level programming language, such as a machine language, or an assembler. The CPU may comprise a set of registers, an arithmetic logic unit (ALU), and a control unit. The control unit is controlled by a sequence of program instructions transferred to the CPU from a program memory. The control unit may contain a number of microinstructions for basic operations. The implementation of the microinstructions may vary, depending on the CPU design. The microprocessor may also have an operating system (a dedicated operating system of an embedded system, or a real-time operating system), which may provide system services to the computer program.

FIG. 10 illustrates a computer program 1000 run on the processor 902. The computer program 1000 may be in source code form, object code form, or in some intermediate form, and it may be stored in a carrier, which may be any entity or device capable of carrying 1002 the program to the apparatus 900. The carrier may be implemented as follows, for example: the computer program 1000 may be embodied on a record medium, stored in a computer memory, embodied in a read-only memory, carried on an electrical carrier signal, carried on a telecommunications signal, and/or embodied on a software distribution medium.

The processor 902 is configured to obtain instantaneous acceleration values representing lower limb motion of a user.

In an embodiment, the instantaneous acceleration values represent tangential lower limb motion of the user. In an embodiment, the instantaneous acceleration values represent foot motion of the user.

The processor 902 is also configured to form an effective acceleration value from the instantaneous acceleration values over a plurality of steps of the user, and to determine a motion parameter representing overall motion of the user by means of the effective acceleration value. For the actual implementation, as illustrated in FIG. 9, the apparatus 900 may comprise an effective acceleration value former 912, and a motion parameter determiner 914. The plurality of steps of the user may refer to a predetermined number of steps. The plurality of steps of the user may also refer to an unknown number of steps taken within a predetermined period such as 5 seconds, or 10 seconds, or any other suitable period during which the user has time to take at least two steps.

In some embodiments, the use of the effective acceleration value may make it possible to measure the energy expenditure or determine the user's speed and/or distance without identifying the taken steps, which simplifies the calculation algorithms and consequently minimizes the energy consumption of the processor 902.

The motion parameter may be a kinetic motion variable representing overall kinematics of the user. The motion parameter may represent kinematic results of a stride, i.e. acceleration, speed, or travelled distance of the user.

Figure 1:
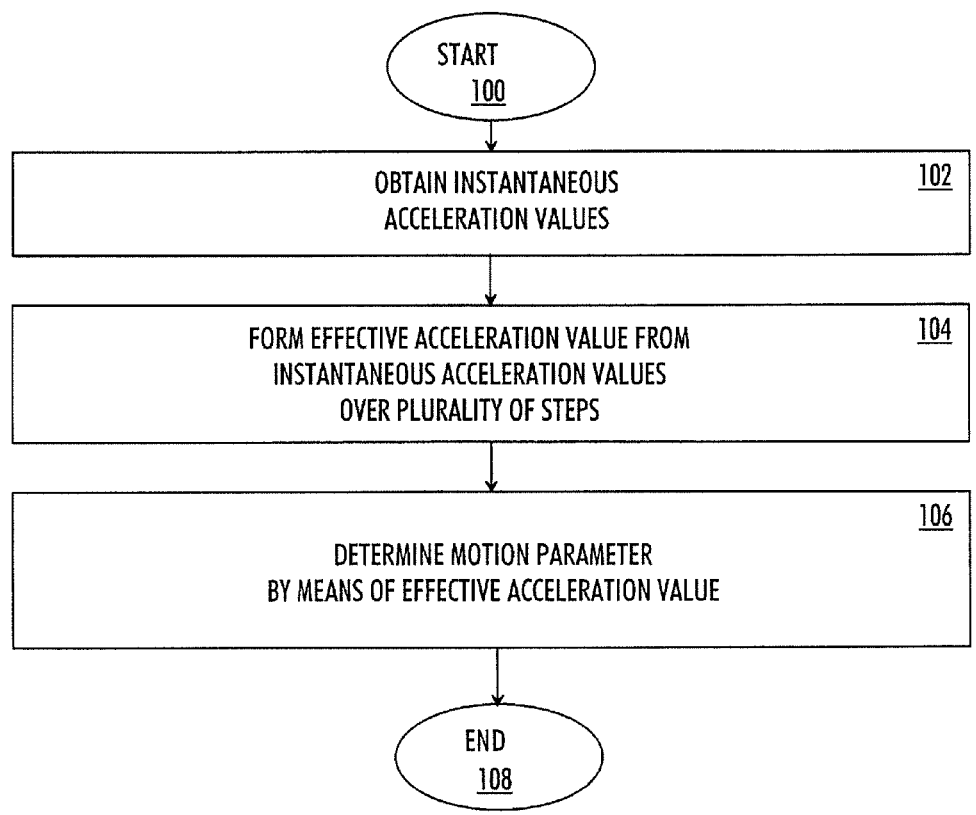
FIGS. 1, 2, 3, and 4 illustrate various embodiments of a method.

Next, a method will be described with reference to FIG. 1. Other functions, not described in this application, may also be executed between the operations or within the operations. Some of the operations or parts of the operations may also be left out or replaced by a corresponding operation or part of the operation. The method starts in 100. In 102, instantaneous acceleration values representing lower limb motion of a user are obtained. In 104, an effective acceleration value is formed from the instantaneous acceleration values over a plurality of steps of the user. In 106, a motion parameter representing overall motion of the user is determined by means of the effective acceleration value. The method ends in 108, but before that operations 102, 104, and 106 may be iterated as long as necessary. The embodiments of the apparatus may also be used to enhance the method.

In an embodiment, the processor 902 may be configured to determine the motion parameter representing the overall motion of the user by means of the effective acceleration value in such a manner that a first functional dependence of the motion parameter is applied to the effective acceleration value if walking motion is identified, and a second functional dependence of the motion parameter is applied to the effective acceleration value if running motion is identified, wherein $M_W$=Walking Motion, $M_E$=Running Motion and $\langle a \rangle$=effective acceleration value Examples of functional dependencies:

$$M_W = \langle a \rangle \times f_{1W} + f_{2W} \text{ for walking, and}$$

$$M_E = \sqrt{\langle a \rangle} \times f_{1R} + f_{2R} \text{ for running,}$$

where the scaling factors are:

a multiplicative factor (the first scaling factors $f_{1W}$ and $f_{1R}$, whereby $F_{1W}$ represents a first functional dependency value that is applied to the effective acceleration value if walking motion is identified and $F_{1R}$ represents a second functional dependency value that is applied to the effective acceleration value if running motion is identified), and an offset scaling factor (the second scaling factors $f_{2W}$ and $f_{2R}$).

Figure 7:
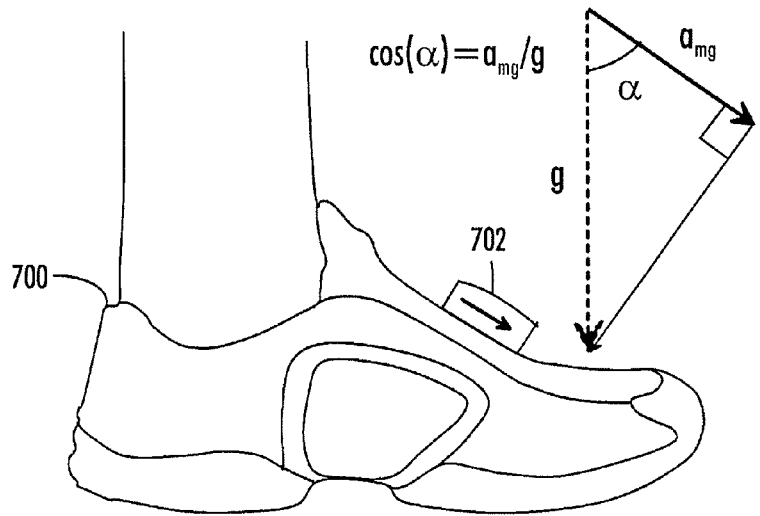
FIGS. 7 and 8 illustrate acceleration measurement from a lower limb.
Figure 8:
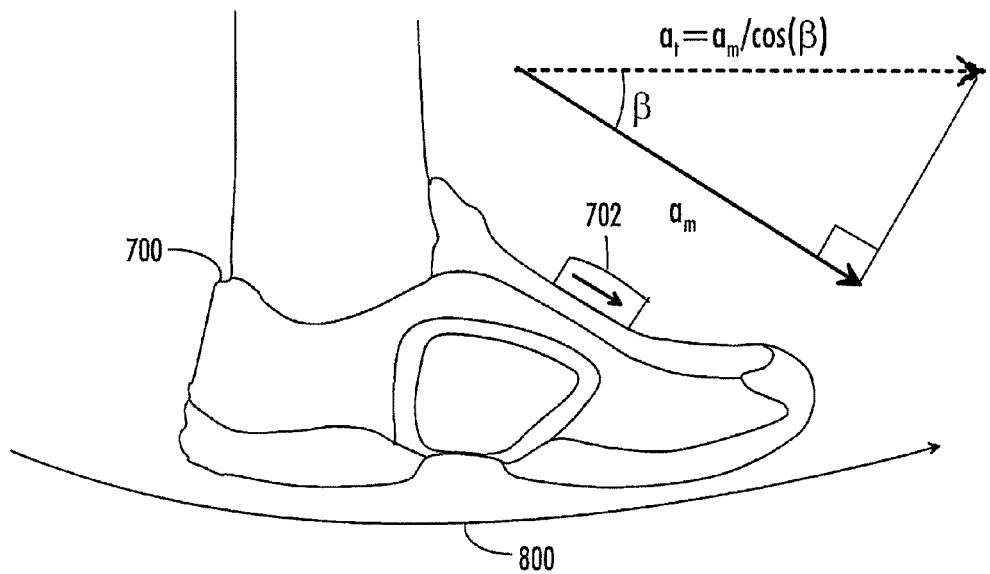

With reference to FIGS. 7 and 8, let us examine the geometry of the motion measurement and the physical interpretation of the scaling factors. FIGS. 7 and 8 illustrate acceleration measurement from a lower limb. A user is wearing a shoe 700, and an apparatus 702 is attached to the shoe 700. The apparatus 702 may be a shoe-mounted stride sensor 1108 as illustrated in FIG. 11. In this example, a one-dimensional accelerometer is used. The measurement direction of the accelerometer is denoted with an arrow drawn inside the apparatus 702. In the measurement direction, the accelerometer typically has the highest sensitivity to acceleration relative to other directions.

FIG. 7 illustrates calibration of the apparatus according to an embodiment: value $a_{mg}$ in the measurement direction represents a projection of Earth's gravity g (approximately 9.81 m/s$^2$) when the user is standing still, i.e. it is a static state of a foot where the foot is not in motion. The angle α between the measurement direction and the direction of Earth's gravitation field may be obtained from the projection $a_{mg}$ and g as follows $$\cos(\alpha) = \frac{a_{mg}}{g} \quad (1)$$

After the calibration of FIG. 7, the actual measurement may be started as illustrated in FIG. 8. While walking or running, the lower limbs of the user move so that the forward motion 800 of the shoe 702 resembles the motion of a pendulum. In the measurement direction, a projection $a_m$ of the actual forward advancement direction acceleration $a_t$ is superimposed with the projection acceleration $a_{mg}$ of the acceleration of Earth's gravity. Thus, the actual forward advancement direction acceleration $a_t$ may be obtained from equation $$a_t = a_m \times \sqrt{1 - \left(\frac{a_{mg}}{g}\right)^2} - a_{mg}\sqrt{1 - \left(\frac{a_{mg}}{g}\right)^2} = a_m \times f_2 + f_1 \quad (2)$$

Equation 2 indicates that the first scaling factor $f_1$ and the second scaling factor $f_2$ have a common scaling factor $$\sqrt{1 - \left(\frac{a_{mg}}{g}\right)^2}$$

which may be obtained when the foot is in the static state by measuring $a_{mg}$. Equation 2 shows that a common scaling factor is possible. However, the scaling factors $f_1$ and $f_2$ may be treated as independent factors and they can also be determined with a calibration procedure where the user runs/walks in order to obtain a reference distance/speed from an external source and inputs the scaling factors or related information to the apparatus 900.

The calibration principle according to FIG. 7 may be applied to a case, where a multi-dimensional accelerometer is applied and thus acceleration values are measured in two or more directions. The scaling factors may be introduced for linear combinations of the components of the acceleration values.

Figure 2:
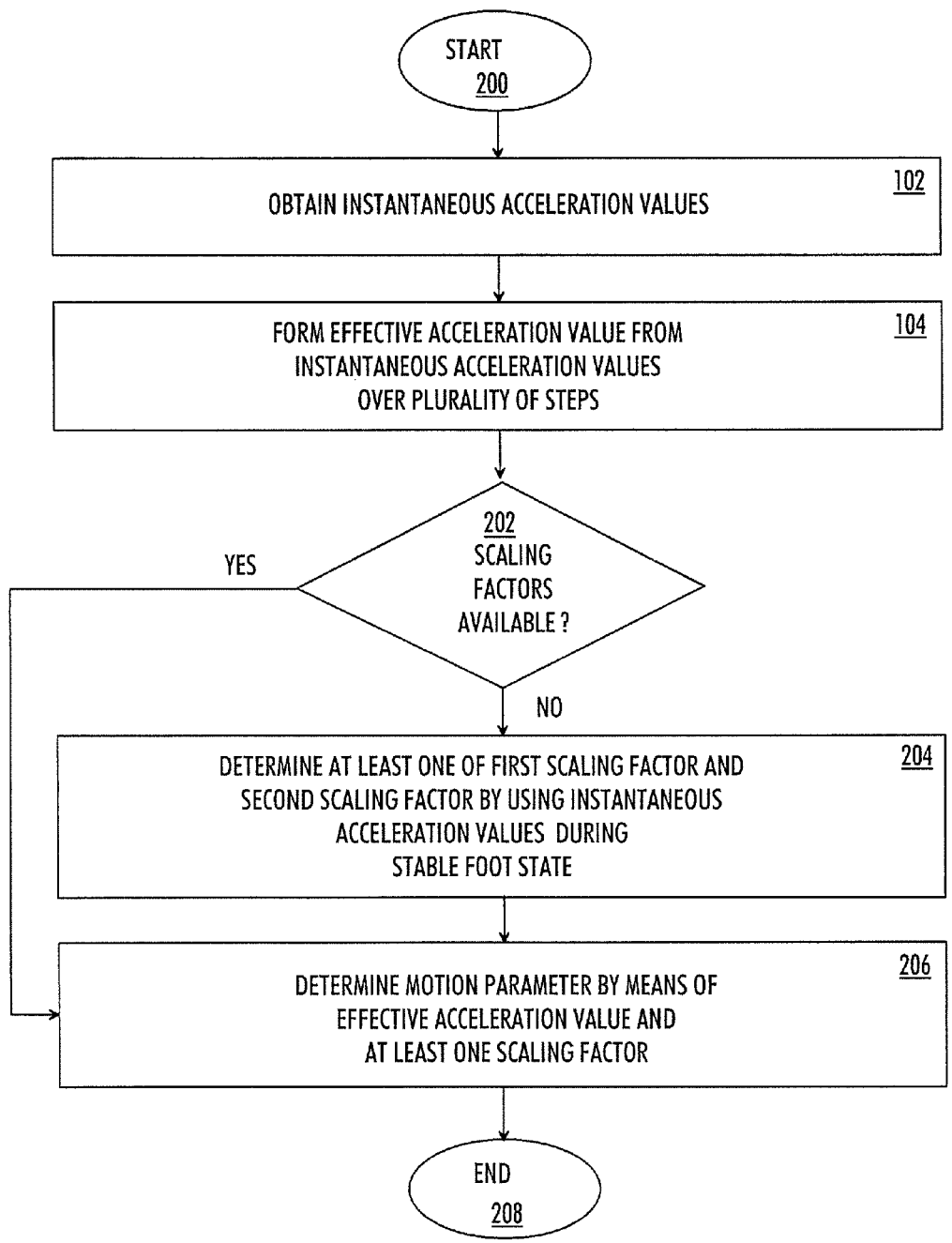
Figure 3:
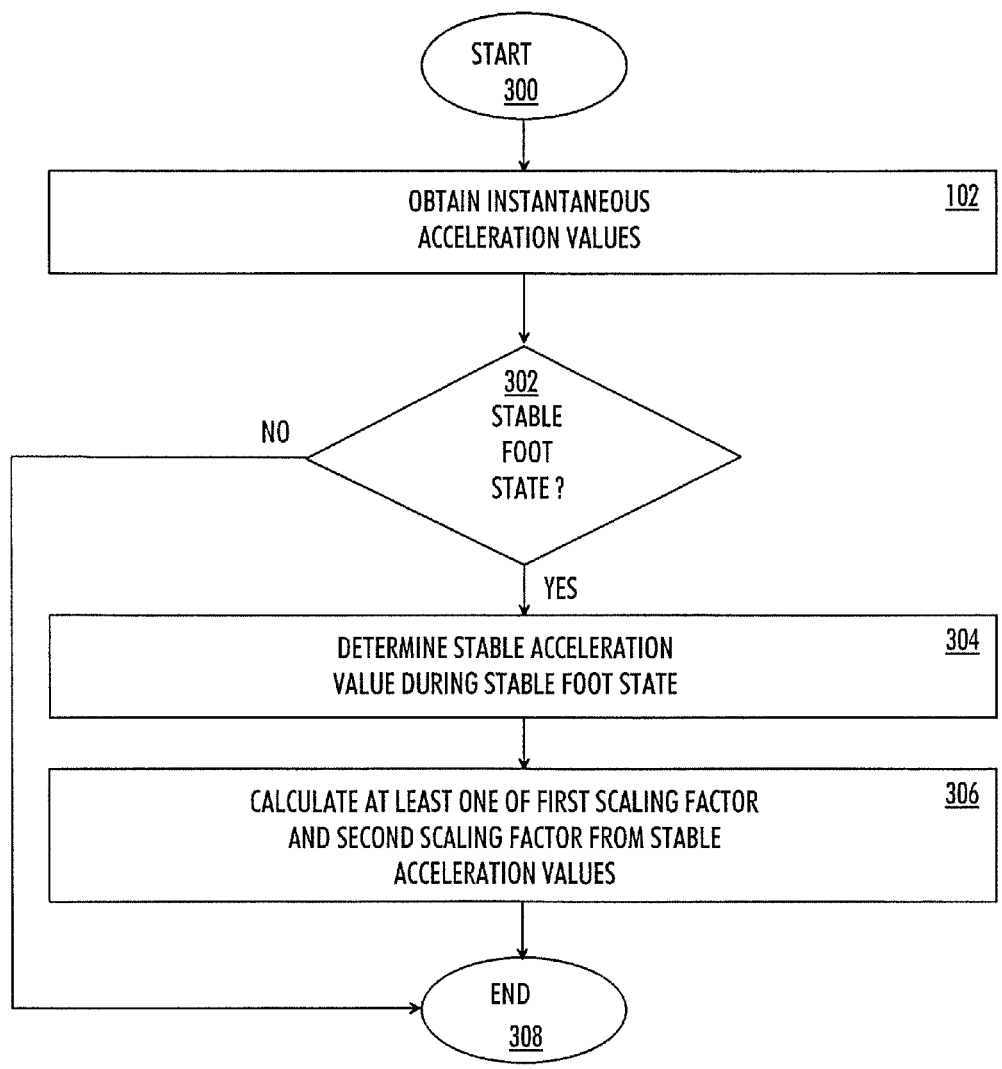
Figure 4:
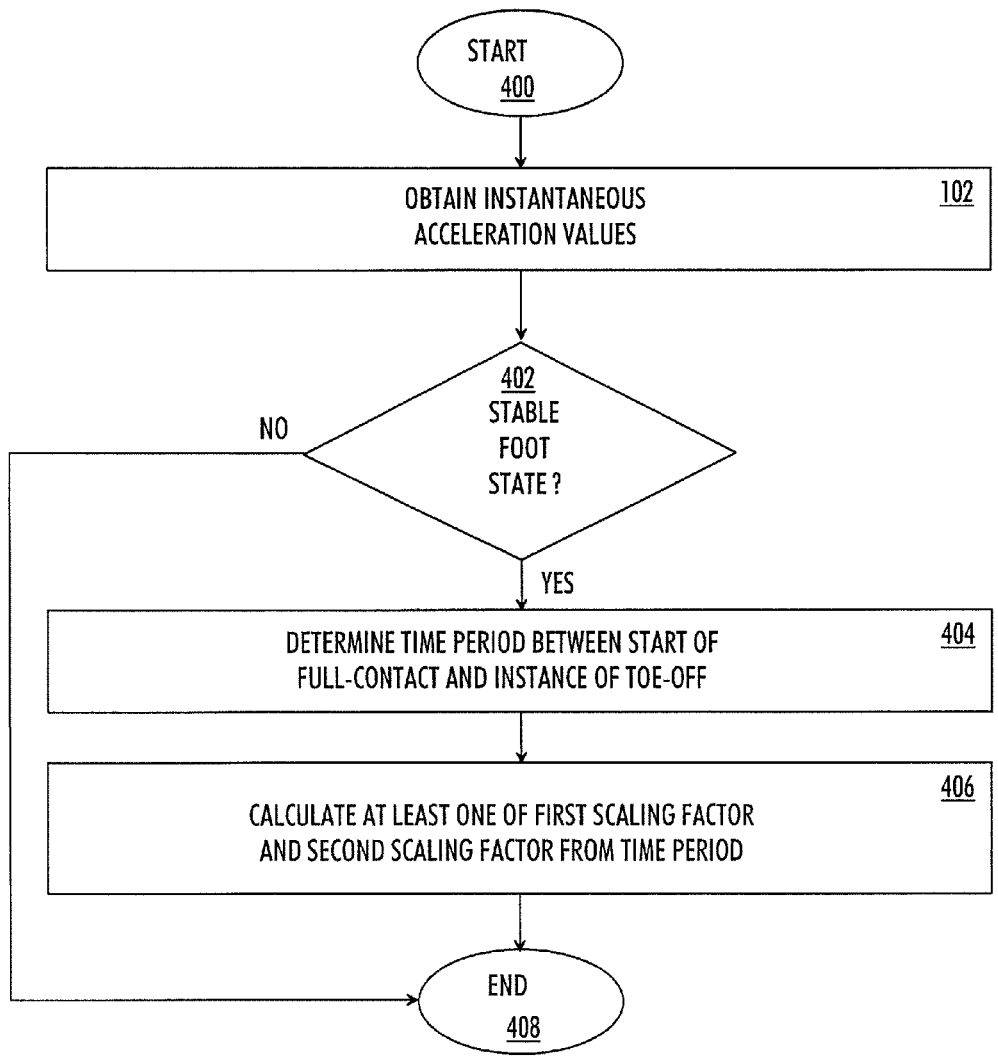

FIGS. 2, 3, and 4 illustrate various embodiments relating to the use of scaling factors.

In FIG. 2, method starts in 200 and ends in 208. Operations 102 and 104 are as in FIG. 1.

In 202, it is checked whether scaling factors are available. If they are not available, 204 is entered, otherwise 206 is entered. The availability of the scaling factors may be checked by the processor 902 and the computer program 1000.

In 204, at least one of a first scaling factor and a second scaling factor is determined by using instantaneous acceleration values during a stable foot state, wherein the first scaling factor provides offset to the motion parameter and the second scaling factor provides a multiplicative for the instantaneous acceleration. The stable foot state 616, illustrated in FIG. 6, may be defined as a time period between a heel strike event and a toe off event in walking. The processor 902 may detect the stable foot state from the instantaneous acceleration values.

In 206, the motion parameter determining operation 106 is expanded so that it further comprises using at least one of a first scaling factor and a second scaling factor, wherein the first scaling factor provides offset to the motion parameter and the second scaling factor provides scaling for the instantaneous tangential acceleration.

In FIG. 3, the method starts in 300 and ends in 308. The operation 102 is as in FIG. 1. FIG. 3 actually describes one way the operation 204 of FIG. 2 may be implemented.

In 302, it is checked whether the foot state is stable. If it is stable, 304 is entered, otherwise the method ends in 308.

In 304, a stable acceleration value is determined during a stable foot state.

In 306, at least one of the first scaling factor and the second scaling factor is calculated from the stable acceleration value.

In FIG. 4, the method starts in 400 and ends in 408. The operation 102 is as in FIG. 1. FIG. 4 actually describes another way the operation 204 of FIG. 2 may be implemented.

In 402, it is checked whether the foot state is stable. If it is stable, 404 is entered, otherwise the method ends in 408.

In 404, a time period between the start of full-contact of the foot and the instance of toe-off of the foot during walking is determined from the instantaneous tangential acceleration values.

In 406, at least one of the first scaling factor and the second scaling factor is calculated from the time period.

The instantaneous acceleration values represent acceleration values recorded at consecutive coordinate points along a foot trajectory during a foot motion or during a stable foot state. An instantaneous acceleration value may represent an average acceleration between two digital sampling points.

In an embodiment, the instantaneous acceleration values are substantially tangential acceleration values where the tangential direction refers to the direction of the foot trajectory when the foot is bent from the knee. The tangential direction is illustrated with reference numeral 800 in FIG. 8. In this case, the measurement direction is fixed relative to the shoe 700. This definition is provided in the user-fixed coordinate system, while the actual acceleration measurement takes place in a moving coordinate system. However, the user-fixed coordinate system definition for the acceleration measurement directions is appropriate.

The desired direction for the measurement, such as the tangential direction, may be obtained by suitably designing a mechanical attachment structure between the stride sensor and a foot, and by fixing the measurement direction within the stride sensor so that the tangential direction becomes the primary measurement direction. Deviations from the desired measurement may be corrected with the scaling factors $f_1$ and $f_2$ if necessary.

Figure 5:
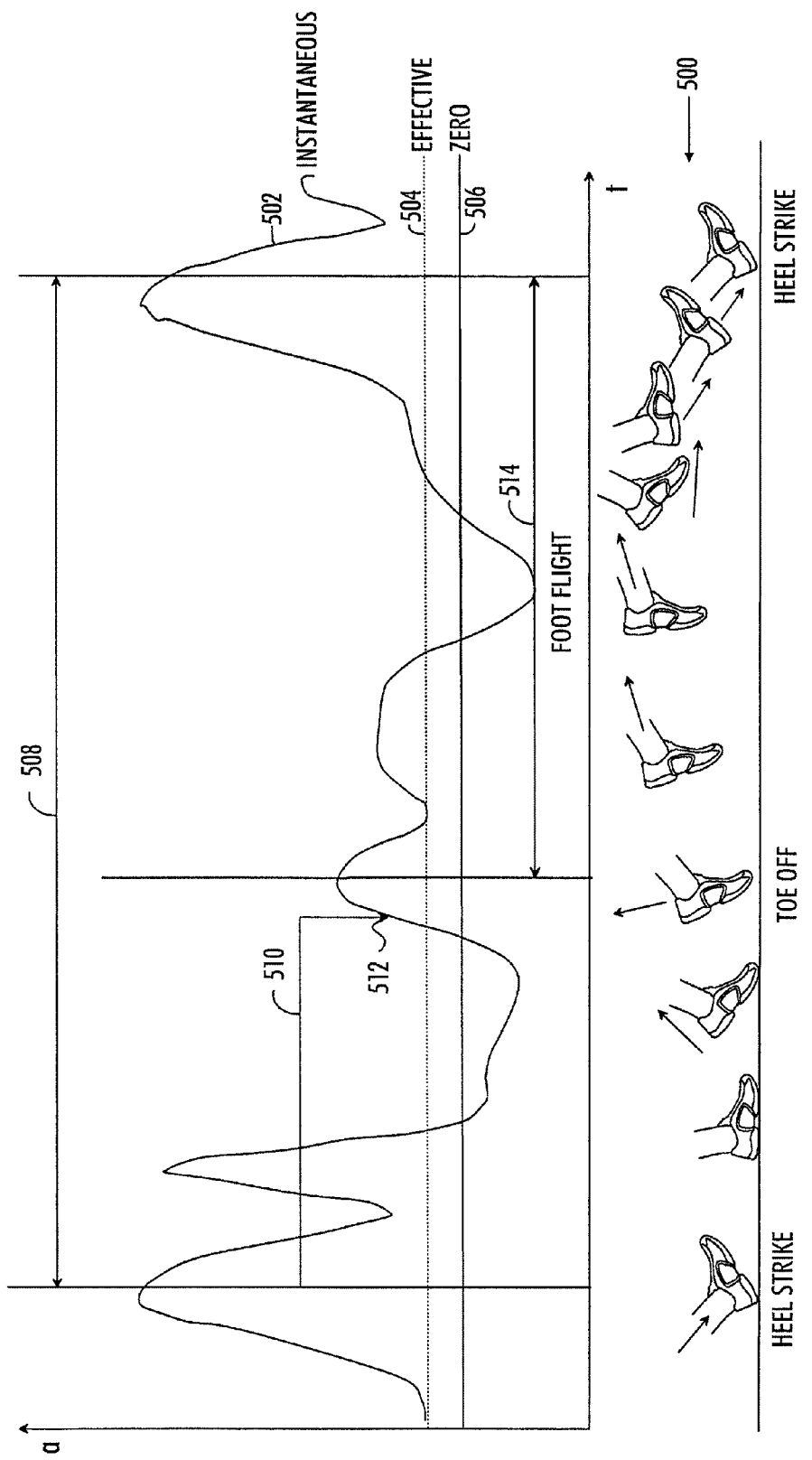
FIG. 5 illustrates acceleration values of running.
Figure 6:
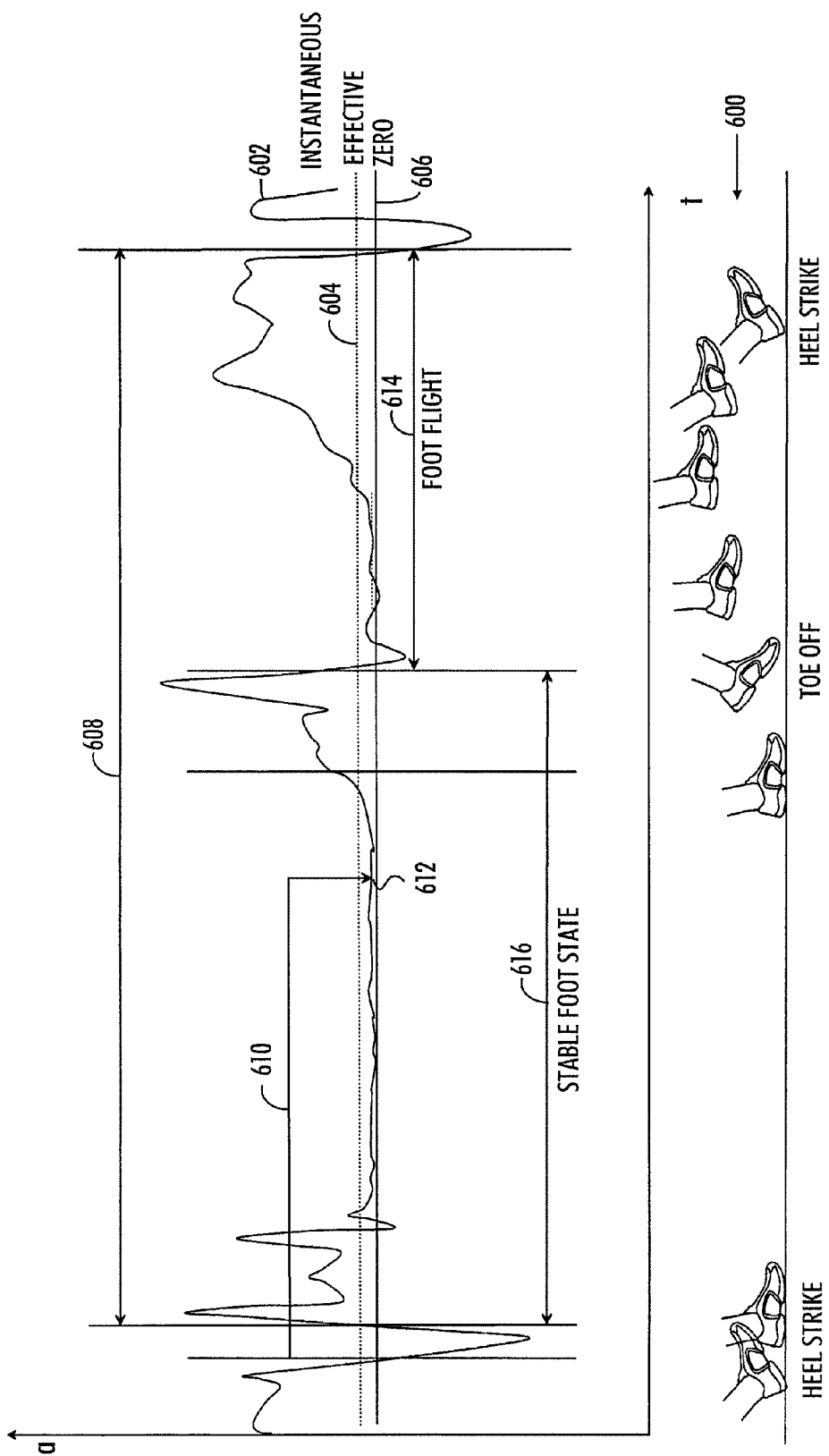
FIG. 6 illustrates acceleration values of walking.

FIGS. 5 and 6 illustrate acceleration values according to some embodiments.

FIG. 5 illustrates acceleration values of running. The X-axis t illustrates time, and Y-axis a illustrates acceleration values. The X-axis t illustrates a sequence 500 of the lower limb movement, from a heel strike event to another heel strike event. The sequence 500 illustrates one step of one foot, which corresponds to a pair of steps. A line 506 illustrates the zero level of acceleration values. A curve 502 illustrates instantaneous acceleration values. A dashed line 504 illustrates effective acceleration values.

An effective acceleration value over a plurality of steps represents the effect of the acceleration of the lower limb when observed for a time period longer than one pair of steps.

In an embodiment, the effective acceleration value represents an average of the instantaneous acceleration values over a plurality of steps.

The use of average provides the advantage that the calculation requires relatively low processing power, which in turn saves the battery power of the apparatus 900.

In an embodiment, the processor 902 is configured to obtain instantaneous foot-flight (514, 614) acceleration values representing lower limb motion of a user and to form an effective acceleration value from the instantaneous foot-flight acceleration values over a plurality of steps of the user. Furthermore, the processor 902 is further configured to determine a motion parameter representing overall motion of the user by means of the effective acceleration value. In this manner, the instantaneous acceleration values are used partially so that only a foot-flight (514, 614) phase is considered. The foot-flight (514, 614) phases of consecutive steps are used to calculate the effective acceleration values so that the observation period spans more than a time period of a step.

The processor 902 may identify instantaneous foot-flight (514, 614) acceleration values on the basis of the time structure of the instantaneous acceleration values. In an embodiment, the processor 902 applies a pattern recognition algorithm for identifying the instantaneous foot-flight (514, 614) acceleration values.

In an embodiment, the processor 902 is configured to form the effective acceleration value by calculating autocorrelation for the instantaneous acceleration values.

In an embodiment, the effective acceleration values are calculated in a moving window which spans a time period longer than one pair of steps.

FIG. 6 illustrates acceleration values of walking. Again, the X-axis t illustrates a sequence 600 of the lower limb movement, from a heel strike event to another heel strike event, and the Y-axis a illustrates acceleration values as a function of time. A line 606 illustrates the zero level of acceleration values. A curve 602 illustrates instantaneous acceleration values. A dashed line 604 illustrates effective acceleration values.

The raw data representing instantaneous acceleration values may be high-pass filtered in order to reduce low frequencies in the signal. In an embodiment, the instantaneous acceleration values may be filtered out above a predetermined threshold. This filtering reduces an offset to the effective acceleration values due to the heel-strike phase and resulting parasitic signals of steps.

In connection with the described embodiments, or in a totally independent fashion regardless of the embodiments, analysis of instantaneous acceleration values 502, 602 may be used to identify whether the user is running or walking. This is implemented so that the processor 902 is configured to obtain instantaneous acceleration values in a predetermined time point of a step period 508, 608. A predetermined time point may be a predetermined offset 510, 610, such as a predetermined time period starting from the heel strike or another recognizable signal phase. The processor 902 is configured to identify whether the user is running or walking by analysis of the instantaneous acceleration values in the predetermined time point 512, 612. In an embodiment of the invention, the predetermined offset 510, 610 is selected so that in walking, the predetermined time point 612 falls into the stable foot state whereas in running, the predetermined point 512 falls outside the stable foot state. The selection is based on the fact that the duration and the location of the stable foot state in walking can be predicted accurately, and the predetermined point 612 can be fixed to a predetermined value, such as 30 % of the step period 608 measured from a heel-strike in order to obtain instantaneous acceleration values reliably from the stable foot state. In running, the predetermined point 512 falls outside a stable foot state with the corresponding predetermined offset 510.

The effective acceleration value in the predetermined time point may be compared to a predetermined acceleration threshold, for example: if the effective acceleration value in the predetermined time point 512, 612 is smaller than the predetermined acceleration threshold, the user is walking, or else (i.e. the effective foot-flight (514, 614) acceleration value is equal to or greater than the predetermined acceleration threshold) the user is running.

Instantaneous acceleration values may be formed by a suitable measurement sensor 904, 908. In principle, the measurement sensor 904, 908 measures a physical quantity and converts it into a signal received by the processor 902.

The apparatus 900 may further comprise an instantaneous acceleration value input interface 910 capable of receiving the instantaneous acceleration values. Naturally, the input interface 910 may be implemented as a single component or as multiple components.

As illustrated in FIG. 9, the measurement sensor may be an internal measurement sensor 908, which is physically coupled with the apparatus 900. The internal sensor 908 may be coupled 924 with the interface 910 by a wiring on a printed circuit board, for example.

The measurement sensor may also be a wireless external sensor 904. The wireless external sensor may be coupled 920 by electric and/or magnetic radiation with a receiver 906 of the apparatus 900, and the receiver 906 (implemented by an integrated circuit, for example) may be coupled 922 with the interface 910 by a wiring on a printed circuit board.

The communication by the wireless external sensor 904 may be implemented with an induction-based technology utilizing a magnetic field, or a radio-based technology utilizing electric radiation, for example. It is to be noted that both technologies involve both the magnetic field and the electric radiation, but the separation is based on the fact that either one of these physical phenomena predominates and is only used for the communication in each technology. The induction-based transmission may operate at a kilohertz range frequency (5 kilohertz, 125 kilohertz, or over 200 kilohertz, for example). The radio transmission may utilize a proprietary transceiver (operating at a 2.4 gigahertz frequency, for example), or a Bluetooth transceiver, for example. Emerging ultra low power Bluetooth technology may be used, as its expected use cases include heart rate monitoring. The transmission of the instantaneous acceleration values may utilize any suitable protocols: the principles of time division and/or packet transmission, for example.

The measurement sensor 904, 908 typically comprises an accelerometer and an analog-to-digital (AD) converter.

The accelerometer measures its own motion, acceleration, i.e. the rate of change of velocity, and converts the acceleration into an electric signal. The electric signal is converted into a digital format in the AD converter. Acceleration can be expressed by the unit of measurement g. One g is the acceleration caused to an object by Earth's gravity. Accelerations between −2 to +2 g can usually be measured from human movement. Due to its implementation, the accelerometer may belong to microelectromechanical systems (MEMS).

Various techniques may be used for measuring acceleration. Piezo-resistor technology employs material whose resistance changes as it compresses. The acceleration of mass produces a force in a piezo resistor. If constant current is supplied through the piezo resistor, its voltage changes according to the compression caused by acceleration. In piezo-electric technology, a piezo-electric sensor generates charging when the sensor is accelerated. In silicon bridge technology, a silicon chip is etched so that a silicon mass remains on it at the end of a silicon beam. When acceleration is directed to the silicon chip, the silicon mass focuses a force on the silicon beam, thus changing the resistance of the silicon beam. Micro-machined silicon technology is based on the use of a differential capacitor. Voice coil technology is based on the same principle as a microphone. Examples of suitable movement sensors are: Analog Devices ADXL105, Pewatron HW or VTI Technologies SCA series. The implementation of the accelerometer may also be based on other appropriate techniques, for example on a gyroscope integrated into a silicon chip or on a micro vibration switch incorporated into a surface mounting component.

It is also to be noted that the accelerometer may measure the acceleration in one, two or three dimensions. A multi-dimensional measurement may be carried out with a single accelerometer component having a multi-dimensional capability. In another embodiment, two or even three separate accelerometers are applied, each measuring a different dimension. European patent application 1 066 793 describes the use of at least a pair of accelerometers, which may be mounted on an athletic shoe, for example.

In summary, the apparatus 900 illustrated in FIG. 9 may be the wrist receiver 1102 of FIG. 11, or the shoe-mounted stride sensor 1108 of FIG. 11, for example. The acceleration measurement sensor 904, 908 may thus process the instantaneous acceleration values received from the accelerometer in order to obtain the effective acceleration value, or it may transfer them to another apparatus for processing in order to obtain the effective acceleration value.

In an embodiment, the instantaneous acceleration values comprise at least two acceleration vector components. The processor 902 may be configured to form a scalar representation of the at least two acceleration vector components, and to form the effective acceleration value from the scalar representation over the plurality of the steps of the user.

Let us suppose that the acceleration vector components are $a_x$, $a_y$, $a_z$ which correspond to acceleration in an orthogonal x, y, z coordinate system. By forming the scalar representation, superposition of the acceleration vector components is calculated, and the direction information of the vectors vanishes. For example, a scalar representation of vectors $a_x$, $a_y$, $a_z$ is $$a=\sqrt{a_x^2+a_y^2+a_z^2} \quad (3)$$

The motion variable is calculated from the effective value of the scalar representation. The advantage of using the scalar representation and the resulting effective acceleration value is that the scalar representation is less sensitive to the orientation of a stride sensor when fixed to a foot. Thus, there is less need for calibration in each exercise session than when not using the scalar representation.

It will be obvious to a person skilled in the art that as technology advances, the inventive concept can be implemented in various ways. The invention and its embodiments are not limited to the examples described above but may vary within the scope of the claims.

What is claimed is:

1. An apparatus comprising:
an accelerometer configured to measure instantaneous acceleration values representing lower limb motion of a user, a processor configured to process said instantaneous acceleration values, wherein the instantaneous acceleration values comprise at least two orthogonal acceleration vector components, the processor being configured to form a scalar representation of the at least two orthogonal acceleration vector components and to form an effective acceleration value using only the scalar representation over a plurality of steps of the user without using direction information associated with the orthogonal acceleration vector components, the processor being further configured to determine a motion parameter representing overall motion of the user by using the effective acceleration value, thereby reducing sensitivity to orientation of the apparatus and reducing a need for calibration of the apparatus.

2. The apparatus of claim 1, wherein the scalar representation of an acceleration a is formed with the at least two orthogonal acceleration vector components $a_x$, $a_y$, $a_z$ using formula $a=\sqrt{a_x^2+a_y^2+a_x^2}$; and
the processor being configured to form the effective acceleration value from the scalar representation over the plurality of the steps of the user.

3. The apparatus of claim 1, wherein the instantaneous acceleration values represent tangential lower limb motion of the user.

4. The apparatus of claim 1, wherein the instantaneous acceleration values comprise instantaneous foot-flight acceleration values, the processor being further configured to form the effective acceleration value from the instantaneous foot-flight acceleration values over the plurality of the steps of the user.

5. The apparatus of claim 1, wherein the processor is further configured to determine the motion parameter representing the overall motion of the user by means of the effective acceleration value in such a manner that a first functional dependence value of the motion parameter is applied to the effective acceleration value if walking motion is identified, a second functional dependence value of the motion parameter being applied to the effective acceleration value if running motion is identified.

6. The apparatus of claim 1, wherein the apparatus is a mobile apparatus, a sports computer, a running computer, a multi-sports computer, an activity monitor, a pedometer, a foot-pod, a shoe-mounted stride sensor, a measurement unit attachable to a lower limb of the user, and/or a subscriber terminal of a radio system.

7. A method to determine overall motion of a user, the method comprising:
measuring with an accelerometer instantaneous acceleration values representing lower limb motion of a user, wherein the instantaneous acceleration values comprise at least two orthogonal acceleration vector components;
forming using a processing device a scalar representation of the at least two orthogonal acceleration vector components;
forming using said processing device an effective acceleration value using only the scalar representation over a plurality of steps of the user without using direction information associated with the orthogonal acceleration vector components; and determining a motion parameter representing overall motion of the user by using the effective acceleration value, thereby reducing sensitivity to orientation of the apparatus and reducing a need for calibration of the apparatus.

8. The method of claim 7, the method further comprising: forming the scalar representation of an acceleration a with at least two acceleration vector components $a_x$, $a_y$, $a_z$ using formula $a=\sqrt{a_x^2+a_y^2+a_z^2}$; and forming the effective acceleration value from the scalar representation over the plurality of the steps of the user.

9. The method of claim 7, wherein the instantaneous acceleration values represent tangential lower limb motion of the user.

10. The method of claim 7, wherein the instantaneous acceleration values comprise instantaneous foot-flight acceleration values, the method further comprising forming the effective acceleration value from the instantaneous foot-flight acceleration values over the plurality of the steps of the user.

11. The method of claim 7, wherein the motion parameter representing the overall motion of the user is determined by means of the effective acceleration value in such a manner that a first functional dependence value of the motion parameter is applied to the effective acceleration value if walking motion is identified, a second functional dependence value of the motion parameter being applied to the effective acceleration value if running motion is identified.

12. An apparatus to determine overall motion of a user, the apparatus comprising:
    an accelerometer to measure instantaneous acceleration values representing lower limb motion of a user, wherein the instantaneous acceleration values comprise at least two orthogonal acceleration vector components;
    a processing device that performs operations comprising:
    forming a scalar representation of the at least two orthogonal acceleration vector components;
    forming an effective acceleration value using only the scalar representation over a plurality of steps of the user without using direction information associated with the orthogonal acceleration vector components;
    and determining a motion parameter representing overall motion of the user by using the effective acceleration value, thereby reducing sensitivity to orientation of the apparatus and reducing a need for calibration of the apparatus.

13. A non-transitory computer-readable medium, comprising instructions which, when executed by a mobile apparatus, cause the mobile apparatus to: measure instantaneous acceleration values representing lower limb motion of a user using an accelerometer, wherein the instantaneous acceleration values comprise at least two orthogonal acceleration vector components;
    form a scalar representation of the at least two orthogonal acceleration vector components using a processing device;
    form an effective acceleration value from using only the scalar representation over a plurality of steps of the user without using direction information associated with the orthogonal acceleration vector components using said processing device; and determine using said processing device a motion parameter representing overall motion of the user by using the effective acceleration value, thereby reducing sensitivity to orientation of the apparatus and reducing a need for calibration of the apparatus.

14. The non-transitory computer-readable medium of claim 13, the computer-readable medium comprising instructions which when executed by the mobile apparatus, cause the mobile apparatus to:
    form the scalar representation of an acceleration a with at least two acceleration vector components $a_x$, $a_y$, $a_z$ using formula $a=\sqrt{a_x^2+a_y^2+a_z^2}$; and
    form the effective acceleration value from the scalar representation over the plurality of the steps of the user.

15. The non-transitory computer-readable medium of claim 13, wherein the instantaneous acceleration values represent tangential lower limb motion of the user.

16. The non-transitory computer-readable medium of claim 13, wherein the instantaneous acceleration values comprise instantaneous foot-flight acceleration values, the instructions which when executed by the mobile apparatus, cause the mobile apparatus to form the effective acceleration value from the instantaneous foot-flight acceleration values over the plurality of the steps of the user.

17. The non-transitory computer-readable medium of claim 13, wherein the motion parameter representing the overall motion of the user is determined by means of the effective acceleration value in such a manner that a first functional dependence value of the motion parameter is applied to the effective acceleration value if walking motion is identified, a second functional dependence value of the motion parameter being applied to the effective acceleration value if running motion is identified.

* * * * *